United States Patent [19]

Lutz

[11] 4,317,938

[45] Mar. 2, 1982

[54] PREPARATION OF SECONDARY ALKANOL ALKOXYLATES

[75] Inventor: Eugene F. Lutz, Houston, Tex.

[73] Assignee: Shell Oil Company, Houston, Tex.

[21] Appl. No.: 221,955

[22] Filed: Dec. 31, 1980

[51] Int. Cl.$^3$ ............................................. C07C 41/01
[52] U.S. Cl. .................................. 568/619; 568/622; 568/625; 568/678; 568/679; 260/460
[58] Field of Search ............... 568/619, 622, 625, 678, 568/679, 692; 260/460

[56] References Cited

U.S. PATENT DOCUMENTS

| | | |
|---|---|---|
| 1,614,883 | 1/1927 | Davidson . |
| 2,520,611 | 8/1950 | Roberts et al. |
| 2,520,612 | 8/1950 | Roberts et al. |
| 2,640,070 | 5/1953 | Dahmen ............................. 260/460 |
| 2,870,220 | 1/1959 | Carter . |
| 4,226,797 | 10/1980 | Bakker et al. ....................... 260/460 |

OTHER PUBLICATIONS

"Formation of Mixed Ethers by the Action of Sulfates on Alcohols," G. Lagrange et al, *Compt. Rend.*, 254, 1821-1822, (1962), as abstracted in *Chem. Abstracts*, 57, No. 649h.

*Primary Examiner*—Howard T. Mars

[57] ABSTRACT

A process for the preparation of $C_8$ to $C_{20}$ secondary alkanol alkoxylates from $C_8$ to $C_{20}$ olefins and alkylene and/or polyether glycols, which comprises sulfating the olefins with sulfuric acid to obtain $C_8$ to $C_{20}$ secondary monoalkyl sulfuric acids, introducing said monoalkyl sulfuric acids and said glycols into an alkoxylation reaction zone, and reacting said monoalkyl sulfuric acids and said glycols under specified conditions of time and temperature.

6 Claims, 1 Drawing Figure

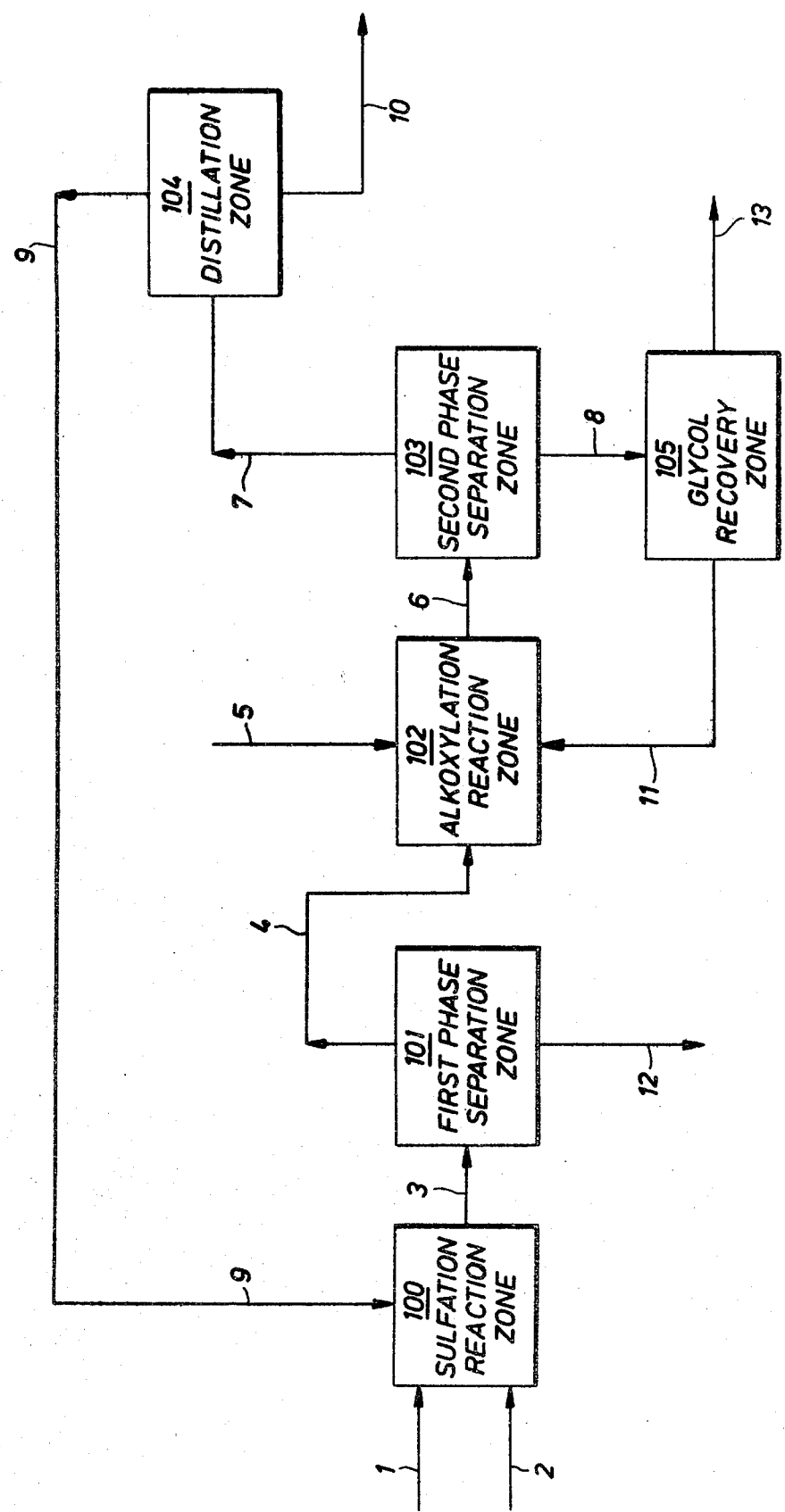

PREPARATION OF SECONDARY ALKANOL ALKOXYLATES

BACKGROUND OF THE INVENTION

This invention relates to a process for the preparation of secondary alkanol alkoxylates. More particularly, the invention relates to the preparation of alkoxylates from $C_8$ to $C_{20}$ olefins, via a process that includes a sulfation step in which the olefins and sulfuric acid are introduced into a reaction zone for preparation of $C_8$ to $C_{20}$ monoalkyl sulfuric acids and an alkoxylation step in which the monoalkyl sulfuric acids and certain alkylene glycols and/or polyether glycols are reacted under specified conditions of temperature and residence time to yield the alkoxylates.

Secondary alkanol alkoxylates, as the terminology is used herein, are compounds of the general formula

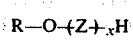

wherein R is secondary alkyl, x is an integer, and Z represents an oxyalkylene group. The alkoxylates of particular interest to the invention include the ethoxylates for which each Z is an oxyethylene group, the propoxylates for which each Z is an oxypropylene or oxyisopropylene group, and mixed alkoxylates having both ethoxy and propoxy ether groups. Compounds of the above formula in which the secondary alkyl portion of the molecule has a carbon number in the detergent range (i.e., $C_8$ to $C_{20}$) and x is an integer greater than about 2, have recognized utility relating to their surfactant properties; the ethoxylate compounds are particularly common as components of industrial detergent formulations. Alkoxylates in which x is an integer greater than or equal to one serve as intermediates in the manufacture of alkoxylates having a longer polyether chain in the molecule, i.e, a higher value of x.

Detergent-range secondary alkanol alkoxylates have heretofore been commercially prepared by the reaction of alkylene oxides with secondary alkanols. Unlike the more common detergent-range primary alkanol alkoxylates, the detergent-range secondary alkanol alkoxylates cannot be readily produced by direct alkaline-catalyzed reaction with the alkylene oxide, but have instead required an initial acid-catalyzed reaction between the alkylene oxide and the secondary alkanol to produce a "seed" alkoxylate, of the above formula with x typically having an average value no greater than about three. Further addition of alkylene oxide to the seed alkoxylate, if desired, can then be accomplished by reaction under alkaline conditions. Conventional processing for the preparation of detergent-range secondary alkanol alkoxylates in this manner is described, for instance, by C. A. Carter in U.S. Pat. No. 2,870,220. The detergent-range secondary alcohols used in the synthesis of alkoxylates under conventional practice have generally been prepared from detergent-range paraffins by oxidation in the presence of a borate catalyst. Relevant to the description of the present invention as a process for the preparation of $C_8$ to $C_{20}$ secondary alkanol alkoxylates from $C_8$ to $C_{20}$ olefins, it is known in the art that detergent-range secondary alkanols can also be prepared from detergent-range olefins by sulfation with concentrated sulfuric acid followed by hydrolysis.

SUMMARY OF THE INVENTION

It has now been found that valuable detergent-range secondary alkanol alkoxylates can be prepared from detergent-range olefins and certain alkylene glycols or polyether glycols by a process which comprises sulfating said olefins by reaction with sulfuric acid to yield detergent-range monoalkyl sulfuric acids and introducing said monoalkyl sulfuric acids and said glycols into an alkoxylation reaction zone for reaction, under specified conditions of temperature and residence time, to the desired alkoxylates.

The alkoxylates of interest are those of formula I,

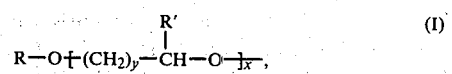

wherein R is secondary alkyl having 8 to 20 carbon atoms, x is an integer from one to about 20, y is the integer one or the integer 2, and R' represents, individually in each occurrence, either hydrogen or methyl, with the proviso that R' is hydrogen when y is 2.

The discovery that such a process can be used to prepare secondary alkanol alkoxylates presents an attractive alternative to conventional methods for production of these known materials. In contrast to prior art methods for manufacture of alkoxylates from detergent-range olefins, the process of the invention does not include a distinct hydrolysis reaction step for preparation of a detergent-range secondary alkanol intermediate. According to the present invention, the monoalkyl sulfuric acids heretofore utilized only in preparation of such an alkanol intermediate can be directly utilized in a single reaction for synthesis of the alkoxylate.

One or more of a number of other processing advantages may also be realized through use of this invention, depending upon the particular starting materials employed and the products desired. For instance, it is possible under the process of the invention to prepare alkoxylates having any desired number of oxyalkylene groups, i.e., those of formula I in which x has any value between 1 and 20, by a single addition reaction, thus eliminating the need for the conventional two reaction step—one acid-catalyzed and one alkaline-catalyzed—method used in the prior art for preparation of certain higher alkoxylates, i.e., having a value of x greater than about 3, from alkanols and ethylene oxide. Furthermore, by accomplishing alkoxylation in the absence of added catalyst, the process of the invention facilitates preparation of an alkoxylate uncontaminated by catalyst residues.

Particular benefit may further be identified relating to the manufacture of specific or narrow-range alkoxylate products, i.e., those in which the bulk of the alkoxylate molecules have the same or nearly the same number of oxyalkylene groups, respectively. It is known in the art that alkoxylate formulations consisting of molecules having a number of ether groups within a relatively narrow range, have very desirable detergency properties. Only a relatively broad-range product can be obtained by conventional commercial techniques for alkoxylate manufacture. However, direct addition of specific or narrow-range polyether glycol compounds to a secondary alkyl chain according to the invention results in a narrow-range alkoxylate product.

BRIEF DESCRIPTION OF THE DRAWING

The attached drawing illustrates one particular aspect of the process of the invention in schematic flow diagram form. In the drawing, the two reaction-step process of the invention is shown together with optional steps preferred for treatment of process intermediate and product streams.

DESCRIPTION OF THE PREFERRED EMBODIMENTS

In its most general aspects, the invention relates to a two reaction step method for the conversion of olefin and glycol reactants into the desired detergent-range secondary alcohol alkoxylate.

The olefin reactant suitably comprises in substantial part one or more detergent-range ($C_8$ to $C_{20}$) mono-olefins, which may be internal or alpha-olefins and which may be linear or branched. Either single cut olefins or mixtures of olefins may be used. For reasons relating to desirable surfactant properties of the product alkoxylate, preference is given to olefins in the $C_{10}$ to $C_{18}$ range and also to olefins for which more than about 60 percent of the molecules are of a linear configuration. Illustrative examples of detergent-range olefins suitable for use in the invention include specific compounds, such as decene-1, decene-2, decene-3, dodecene-1, dodecene-2, hexadecene-1, heptadene-3, 2-methyloctene-3, 2,3-dimethyl-decene-5, 4-ethyl-dodecene-1, 2-butyl-tridecene-4, etc., as well as mixtures of olefins, such as the commercially available materials specified as having carbon numbers primarily within various ranges, for instance $C_{11}$ to $C_{12}$, $C_{13}$ to $C_{14}$, and $C_{15}$ to $C_{18}$. For best results, the olefin reactant used in the practice of the invention is substantially free of aromatic and diene compounds.

A necessary step in the process of the invention is the reaction of the detergent-range olefin starting material with concentrated sulfuric acid to obtain detergent-range secondary monoalkyl sulfuric acids. This reaction is generally known in the art, for instance as a means of producing alkyl sulfuric acid salts, which are also common components of detergent formulations. Suitable examples of procedures for accomplishing the preparation of monoalkyl sulfuric acids in this manner are found in U.S. Pat. No. 2,640,070 to Dahmen and also in U.S. Pat. No. 4,226,797 to Bakker et al. The teachings of Dahmen and Bakker et al on olefin sulfation are incorporated herein by reference.

For purposes of the invention, the olefin sulfation step is preferably carried out under certain limited reaction conditions. For instance, reaction temperature is preferably in the range of $-10°$ C. to $50°$ C., more preferably in the range of about $0°$ C. to $40°$ C. Sulfation reaction residence times are most desirably in the one second to one hour range. Longer times are also suitable, particularly at the lower temperatures. Relative quantities of reactants added to the sulfation reaction zone are not critical and may very suitably vary over ranges conventionally utilized, for example 0.5 to 15 mols of sulfuric acid per mole of olefin.

In accordance with the teachings of the Bakker et al patent, there are advantages in carrying out the sulfation reaction with a sulfuric acid reactant of between about 75 and 90 percent by weight (%w). Sulfuric acid concentrations within this range result in a reaction product which contains low levels of by-product impurities and which can be phase separated to remove unreacted sulfuric acid. However, since reaction between detergent-range olefins and sulfuric acid having a concentration below about 90 percent by weight is generally characterized by relatively low rate, it is preferable to add to the reaction mixture a quantity of phase transfer agent, for instance detergent-range secondary alcohol, to accelerate the sulfation of the olefins to the desired detergent-range secondary monoalkyl sulfuric acids. Thus, for purposes of this invention, between about 5 and 200 percent by mol of detergent-range secondary alcohol is preferably added to the sulfation reaction zone, calculated on the quantity of detergent-range olefins added to this zone, when operating with an acid concentration of less than about 90%w. As is known in the art, other reaction solvents or accelerating agents may be added to the sulfation reaction in place of or together with detergent-range alcohols.

A sulfuric acid reactant having a concentration greater than 90 percent by weight, e.g., between 90 and 98 percent by weight, is also very suitable for purposes of the invention, and may be used in the sulfation reaction either with or without addition of accelerating agents. The use of acid reactant of such high concentration may be preferred in many instances because of the relatively fast reaction rate for which it is responsible.

Carrying out the sulfation reaction under the specified conditions, yields a liquid mixture comprising desired detergent-range monoalkyl sulfuric acid and unreacted olefin and sulfuric acid. The mixture also contains, as a result of its addition to the sulfation reaction zone and/or as a reaction by-product, a quantity of detergent-range secondary alcohol. Other reaction by-products, for instance dialkyl sulfates, may also be present. Suitably, the sulfation reaction product mixture in its entirety may be introduced into the alkoxylation reaction zone for reaction of the monoalkyl sulfuric acid therein with glycol. Alternatively, and preferably, the sulfation reaction mixture is first treated, for example, according to conventional techniques, to separate out one or more of the other components, particularly the unreacted sulfuric acid. The monoalkyl sulfuric acid-containing sulfation reaction mixture may also be treated to remove other principal components, i.e., olefin and alcohol. However, such separation is generally unnecessary—neither of these components has adverse effect upon the subsequent alkoxylation reaction. The presence of the detergent-range secondary alcohol may, in fact, be responsible for an effective net increase in yield of alkoxylate, as the alcohol is also to some extent converted to alkoxylate by reation with glycol in the alkoxylation reaction zone.

Subsequent to the sulfation reaction step for the conversion of detergent-range olefin to monoalkyl sulfuric acid and the optional treatment of the sulfation reaction product mixture to obtain a purified monoalkyl sulfuric acid by removal of unreacted inorganic sulfuric acid and/or other components, the monoalkyl sulfuric acid is next reacted directly with glycol in an alkoxylation reaction zone. The essence of the present invention is believed to lie in the direct synthesis of alkoxylates from glycol and monoalkyl sulfuric acid compounds and further in the use of this reaction as part of a novel approach to the preparation of detergent-range secondary alkanol alkoxylates from detergent-range olefins.

The glycol reactant employed in this step of the process of the invention suitably comprises in substantial part one or more alkylene glycols or polyether glycols of the formula

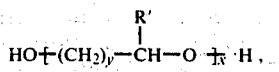

(II)

wherein x is an integer from 1 to about 20, y is the integer 1 or the integer 2, and R' represents, individually in each occurrence, either hydrogen or methyl, with the proviso that R' is hydrogen when y is two. Thus glycol reactant molecules may contain from one to about 20 ether groups, each of which may individually be ethoxy (—CH$_2$—CH$_2$—O—), propoxy (—CH$_2$—CH$_2$—CH$_2$O—), or isopropoxy (—CH$_2$—CH(CH$_3$)—O—). These glycol reactants may also, for convenience, be referred to as selected from the class consisting of C$_2$ and C$_3$ alkylene glycols, i.e., ethylene glycol, 1,2-propanediol and 1,3-propanediol, and also consisting of polyether glycol condensation products of between 2 and about 20 of said alkylene glycols. Particularly good results are obtained using glycol reactants selected from the class consisting of ethylene glycol and 1,3-propanediol and their condensation products, or, in other words, reactants of formula II in which R' is hydrogen. Preferably, the glycol reactant molecules contain from 1 to about 10, more preferably from 1 to about 8, ether groups. From the standpoint of availability and cost of the glycols, those with from 1 to about 4 ether groups are still more preferred reactants. Further reason for preference with regard to the use of the C$_2$ and C$_3$ alkylene glycols and the lower polyether glycols having 2 to 4 ether groups related to higher conversions generally obtainable in reaction with monoalkyl sulfuric acids and higher selectivity to the desired alkoxylate. The alkylene glycols, i.e., compounds of formula II wherein x is one, form a most preferred class of reactants.

Alkylene glycols and polyether glycols suitable for use in the invention are well known and commercially available materials. The lower glycols, e.g., ethylene glycol, diethylene glycol, tetraethylene glycol, propylene glycol, etc., are specifically available, while the higher polyether glycols are typically available as mixtures of compounds having a range of ether groups. Specific or relatively narrow range higher glycols can be obtained from such mixtures, if desired, by distillation.

Preparation of the alkoxylate from the monoalkyl sulfuric acid and glycol can be accomplished simply by mixing in any convenient manner in an alkoxylation reaction zone maintained under specified conditions. The reaction does not require a catalyst or an added reaction solvent.

Temperature is necessarily controlled so that the alkoxylation reaction is substantially carried out within the range of about 100° to 160° C. At lower temperatures, the desired alkoxylation does not proceed at an acceptable rate. At higher temperatures, there is an excessive production of by-products, largely from dehydration or condensation reactions of the glycols. Particular preference is given to temperatures in the range of about 120° to 150° C., while the range of about 130° to 145° C. is considered most preferred. Within the preferred temperature ranges noted, the general observation has been made that conversion of monoalkyl sulfuric acid and glycol decreases and selectivity to the alkoxylate increases as temperature is increased.

Control of average residence time of the glycol reactant and monoalkyl sulfuric acid in the alkoxylation reaction zone is also critical to the successful practice of the process of the invention. Suitable residence times are in the range of about 0.1 to 4 hours. Preference is given to the range of about 0.2 to 2 hours. Relatively short reaction times favor excessive production of secondary alcohols relative to production of the desired alkoxylate, while long reaction times result in reversion of the monoalkyl sulfuric acid to the corresponding detergent-range olefin. Thus, as a rule, within the suitable range of reaction times, extended reaction at a given temperature increases selectivity to the alkoxylate but lowers net conversion of detergent-range olefin in the overall process of the invention.

The ratio of the quantities of glycol and monoalkyl sulfuric acid introduced into the alkoxylation reaction zone is also of importance to the practice of this step of the invention. To achieve acceptable selectivity to the alkoxylate, the glycol reactant should be present in the reaction zone in molar excess over that required for stoichiometric reaction with the monoalkyl sulfuric acid in the zone. An initial molar ratio of glycol to monoalkyl sulfuric acid greater than about three is considered preferred. Generally, cnversion and selectivity in the alkoxylation reaction increase as the molar ratio of glycol to monoalkyl sulfuric acid is increased, up to a ratio of about 20 to 1. While further increases in this ratio are not found to result in significant further increase in conversion or selectivity, such increases in reactant ratio do not appear to have adverse effect on the alkoxylation. Initial glycol to monoalkyl sulfuric acid reactant ratios, based on the quantities of these reactants introduced into the alkoxylation reaction zone, are most preferably in the range of about 6 to 40.

Conditions of pressure under which the alkoxylation reaction may be performed are not critical. It is only necessary that pressure be sufficient to maintain the reactants in the liquid state. Atmospheric and higher pressures are preferred.

The alkoxylation step of the invention is preferably continued until substantially complete conversion of the monoalkyl sulfuric acid, to yield a mixture which typically comprises a substantial quantity of unreacted glycol, as well as the desired alkoxylate product. The reaction mixture also comprises the co-product inorganic sulfuric acid (for the most part in the form of the glycol sulfuric acid which is a reaction product of excess glycol reactant and inorganic sulfuric acid), and contains detergent-range olefin and alcohol both of which may have been carried into the alkoxylation reaction zone along with monoalkyl sulfuric acid from the sulfation reaction and/or formed as by-product from monoalkyl sulfuric acid in the alkoxylation reaction zone.

While the alkoxylate prepared according to the invention is substantially the product of the reaction of one glycol molecule with one molecule of monoalkyl sulfuric acid, it also contains, to a lesser extent, the higher alkoxylate reaction products of multiple glycol molecules with a single molecule of the monoalkyl sulfuric acid. It is believed that in the alkoxylation mixture glycol reactant undergoes self-condensation to higher glycol ethers which then react with monoalkyl sulfuric acid to produce the corresponding higher alkoxylate. To illustrate the most simple situation, if only ethylene glycol is used as glycol reactant, the alkoxylate product formed would substantially be the monoethoxylate of formula I wherein x is one, but there would also be formed lesser quantities of higher ethoxylate, in which the value of x is, for instance, 2, 3, or 4. Typically, under the most preferred process conditions the quantity of alkoxylate that is the reaction product of multiple glycol molecules is only on the order to two to fifteen percent of the total akoxylate product phase produced.

Purification of the product alkoxylate may be accomplished in any convenient manner, for instance, by methods that will be illustrated in the examples of the invention presented herein.

A further and more specific aspect of the invention is a multi-step process for the preparation of detergent-range secondary alkanol alkoxylates from glycol reactant of formula II and olefin compounds of formula I, which comprises:

(a) sulfating, in a sulfation reaction zone, one or more $C_8$ to $C_{20}$ olefins by reaction with sulfuric acid of a concentration between about 75 and 100 percent by weight, thereby obtaining a liquid sulfation reaction product mixture containing $C_8$ to $C_{20}$ monoalkyl sulfuric acids, (b) separating, in a first phase separation zone, said sulfation reaction product mixture into a lower separation phase consisting essentially of inorganic sulfuric acid and an upper separation phase comprising $C_8$ to $C_{20}$ monoalkyl sulfuric acids, (c) introducing said monoalkyl sulfuric acid-containing upper separation phase and said glycol reactant into an alkoxylation reaction zone, (d) reacting the monoalkyl sulfuric acids and the glycol reactant in the alkoxylation reaction zone at a temperature in the range of about 100° to 160° C. for an average residence time of between about 0.1 and 4 hours to obtain a liquid alkoxylation reaction product mixture, (e) separating, in a second phase separation zone said alkoxylation reaction product mixture into a lower separation phase consisting essentially of glycol, inorganic sulfuric acid and glycol sulfuric acid and an upper separation phase comprising $C_8$ to $C_{20}$ alkanol alkoxylates, (f) distilling the upper separation phase of step (e) to obtain an overhead distillation product containing $C_8$ to $C_{20}$ olefins and $C_8$ to $C_{20}$ secondary alchols and a distillation bottoms product comprising alkoxylates, (g) recycling the olefin-containing overhead distillation product to the sulfation reaction zone, (h) treating the lower separation phase of step (e) to recover glycol therefrom, and (i) recycling recovered glycol to the alkoxylation reaction zone.

This specific embodiment of the invention is particularly preferred for the very efficient utilization made therein of various process streams. The embodiment provides means for recovery and recycle of both glycol and olefin reactants. Furthermore, secondary alcohol separated from the alkoxylate product is also recycled to the sulfaction zone where it provides benefit as a phase-transfer agent to increase reaction rate, conversion, and selectivity.

A more detailed description of one such narrow embodiment of the invention is now furnished through reference to the accompanying drawing. It is to be understood that the drawing depicts a number of independent and optional processing steps which are preferred but not necessary to practice of the invention. The illustration which it provides is not intended to limit the broader aspects of the invention. In the process shown, an olefin reactant, designated by the numeral 1, comprising one or more $C_8$ to $C_{20}$ olefins and preferably also one or more $C_8$ to $C_{20}$ secondary alcohols, is introduced into a sulfation reaction zone, designated 100, where it is mixed with concentrated sulfuric acid 2 of between about 75 and 100 percent by weight and reacted under conditions herein specified to yield a sulfation reaction product mixture 3 comprising $C_8$ to $C_{20}$ monoalkyl sulfuric acid, $C_8$ to $C_{20}$ olefin, $C_8$ to $C_{20}$ secondary alcohol and sulfuric acid. In the embodiment of the process of the invention illustrated in the drawing, the mixture 3 is treated to separate sulfuric acid. If the sulfuric acid 2 utilized as reactant in the sulfation reaction of this embodiment of the invention has a concentration less than about 90 percent by weight, this separation may be directly accomplished by phase separation in zone 101. If the acid concentration is above about 90 percent by weight, phase separation is accomplished after addition of a quantity of water to the mixture to bring the concentration below 90%w. In either case, phase separation yields an upper phase comprising essentially all of the monoalkyl sulfuric acid, secondary alcohol, and olefin in the reaction mixture, and a lower phase consisting essentially of sulfuric acid. Phase separation may be accomplished in one or more stages and, if desired, with further addition of water to lower the acid concentration and facilitate more complete removal thereof.

The monoalkyl sulfuric acid, olefin, and alcohol-containing upper liquid phase is withdrawn via line 4 from zone 101 and introduced into alkoxylation reaction zone 102. Glycol reactant 5 is also introduced into zone 102, where it reacts under above-specified conditions with the monoalkyl sulfuric acid to form the desired alkoxylate. The alkoxylation reaction is continued until substantially complete conversion of the monoalkyl sulfuric acid. An alkoxylation product mixture 6 is then withdrawn from zone 102 and introduced into a second phase separation zone 103 wherein the mixture is cooled to less than about 50° C. and allowed to separate into a lower liquid phase, comprising essentially all of the sulfuric acid, glycol, and glycol sulfuric acid in the mixture, and an upper liquid phase comprising substantially all of the detergent-range alkoxylate, olefin, and secondary alcohol. That the glycol reactant can be effectively removed from the alkoxylation reaction mixture by phase separation is considered most advantageous. In prior art alkoxylation processes, the alkylene oxide reactants could be easily distilled from the alkoxylate and alcohol-containing reaction product mixture. However, when glycols as herein specified are utilized as reactants in place of alkylene oxides, it is often the case that the glycols have a volatility about the same as or greater than that of the detergent-range alcohols, olefins, or alkoxylates in the alkoxylation reaction mixture. Distillative separation of the glycols from the detergent-range olefins, alcohols, and alkoxylates is very often not practical.

The upper liquid phase is withdrawn from second phase separation zone 103 as stream 7 and introduced into distillation zone 104. In this distillation zone, olefin and alcohol are stripped from the alkoxylate and taken overhead as stream 9. The olefin/alcohol mixture thus obtained is generally suitable for recycle as olefin reactant to the sulfation zone 100, and is so recycled in the embodiment of the invention illustrated. Under reaction conditions herein specified, the quantity of alcohol in the process, when operated with alcohol recycle, is regulated within acceptable limits by characteristics of its chemical equilibrium with olefin, monoalkyl sulfuric acid, and alkoxylate in the sulfation and alkoxylation reaction zones. Thus, secondary $C_8$ to $C_{20}$ alcohol recycle does not result in excessive buildup of alcohol in the process, and as has been observed, may be desirable for its phase transfer effect on the sulfation reaction. Product alkoxylate is taken from distillation zone 104 as a bottoms stream 10.

The lower liquid phase which is obtained upon separation of the alkoxylation reaction mixture in zone 103, is withdrawn from this zone and introduced into glycol recovery zone 105, where it is treated to separate the glycol and sulfuric acid therein. During alkoxylation in zone 102, excess glycol and sulfuric acid are observed to react to some extent to form an ester product that is also to be found in this lower liquid phase. One suitable means for treatment of the glycol/sulfuric acid/ester mixture 8 in recovery zone 105 comprises heating the mixture in the presence of added water to free the acid and glycol from the ester form, followed by extraction or crystallization to accomplish acid and glycol separation. After its recovery from the acid phase, glycol suitable for reaction with monoalkyl sulfuric acid is withdrawn from zone 105 via line 11 and, in this embodiment of the invention, recycled to alkoxylation zone 102.

Sulfuric acid streams 12 and 13 are withdrawn from the first phase separation zone 101 and the glycol recovery zone 105, respectively. While not depicted as part of the process shown in the drawing, the acid may be recycled to the sulfation reaction zone 100, as sulfuric acid stream 2. However, if it is to be recycled, the recovered acid is first preferably treated to remove contaminants which would otherwise tend to build up in the process stream under conditions of total acid recycle. Particular treatment is generally necessary to concentrate the sulfuric acid stream 13 which typically contains water as the result of the formation of higher alkoxylate as the condensation product of multiple glycol reactant molecules.

The invention, whether in its general aspects or in specific preferred embodiments as described above, may be practiced in either a batch or continuous mode of operation. It is to be understood that in batch operation more than one of the reaction and/or separations steps may be carried out in common processing equipment. For instance, a reactor may be used as the sulfation zone for purposes of the olefin/sulfuric acid reaction, as the first phase separation zone for separation of unreacted sulfuric acid from the sulfation reaction mixture, and also as the alkoxylation reaction zone for reaction between glycol and monoalkyl sulfuric acid. Thus, in the description of the process, the recitation of use of various zones for different process steps is to be interpreted in a functional sense, rather than as relating to distinct items of equipment.

Alkoxylates prepared according to the invention may, if desired, be subjected to still further alkoxylation to increase the length of the hydrophilic polyether chain, i.e., to produce an alkoxylate of formula I having a higher value of x. This may be accomplished, for instance by alkaline catalyzed reaction of the alkoxylate with ethylene oxide, according to procedures known in the art.

Aspects of the process of the invention and certain preferred modes of its operation are further illustrated by the following examples.

EXAMPLE 1

To a 500 ml 3-necked Morton flask, equipped with a high speed paddle stirrer, thermometer, and addition funnel fitted with a drying tube, was added 15.9 g of distilled water and 122.5 g (1.2 m) of 96%w sulfuric acid to give a total of 138.4 g of 85%w sulfuric acid. After cooling to about 12° C., 20.2 g (0.12 m) of a mixture of internal dodecenes was added in 2 minutes to the 85%w sulfuric acid with the temperature at about 12° C. and a stirring speed at 1750 rpm. The reaction temperature rose to 20° C. over 15 minutes and was maintained at 20° C. for an additional 1.75 hrs. The stirrer was stopped and the contents of the flask transferred to a separatory funnel. The upper, organic phase consisting essentially of dodecylsulfuric acid was recovered. A 27.13 g portion of this recovered phase, containing about 0.12 m dodecylsulfuric acid was added to 149.0 g (2.4 m) of dry ethylene glycol at 145° C. in a 3-necked Morton flask, equipped as described above but with the additional funnel replaced by a condenser. As the reaction between ethylene glycol and dodecylsulfuric acid commenced, temperature dropped to 140° C. where it was held for 15 min. The mixture was then cooled rapidly to separate an alkoxylate product phase which was washed twice with 10%w brine and once with a 1%w sodium bicarbonate solution. The product phase, amounting to 18.5 g, was analyzed by gas-liquid chromatography, showing 48.3%m dodecene conversion and a product distribution of 52.7%m secondary dodecanols, 37.1%m secondary dodecanol monoethoxylates, 2.1%m secondary dodecanol diethoxylates, and about 8.1%m of a mixture of by-products, primarily didodecyl ether and dodecene dimers.

EXAMPLE 2-6

Examples 2-6 were performed under the general procedures of Example 1 and are illustrative of the effect of reaction variables on the system. In the case of Examples 4-6, small samples were removed halfway through the ethylene glycol/dodecylsulfuric acid reaction period, washed and analyzed as noted in Example 1.

Process parameters and results of Examples 1-6, particularly the alkoxylation reactions thereof, are further illustrated in the following table:

TABLE 1

Reaction of dodecylsulfuric acid with ethylene glycol

| Example | EG/ASA,[a] | Temp °C. | Time hrs. | Conv.[b] (% m) | Selectivity[c] (% m) | | | |
|---|---|---|---|---|---|---|---|---|
| | | | | | s-$C_{12}$OH | s-$C_{12}$EO-1 | s-$C_{12}$EO-2 | Other |
| 1 | 20 | 140 | 0.25 | 48.3 | 52.7 | 37.1 | 2.1 | 8.1 |
| 2 | 20 | 140 | 0.5 | 44.8 | 40.3 | 47.5 | 3.9 | 8.3 |
| 3 | 20 | 140 | 1.0 | 40.8 | 19.1 | 63.4 | 6.8 | 10.7 |
| 4 | 20 | 150 | 0.5 | 30.0 | 12.0 | 68.4 | 10.6 | 9.0 |
| | | | 1.0 | 26.0 | 5.2 | 69.5 | 13.7 | 11.6 |
| 5 | 20 | 130 | 1.0 | 52.3 | 49.4 | 38.4 | 5.6 | 6.6 |

TABLE 1-continued

| | | Reaction of dodecylsulfuric acid with ethylene glycol | | | | | | |
|---|---|---|---|---|---|---|---|---|
| | | Temp | Time | Conv.[b] | Selectivity[c] (% m) | | | |
| Example | EG/ASA,[a] | °C. | hrs. | (% m) | s-$C_{12}$OH | s-$C_{12}$EO-1 | s-$C_{12}$EO-2 | Other |
| | | | 2.0 | 47.8 | 27.3 | 52.3 | 9.1 | 11.4 |
| 6 | 20 | 120 | 2.0 | 60.8 | 60.1 | 30.2 | 3.7 | 5.9 |
| | | | 4.0 | 59.7 | 39.4 | 40.6 | 5.9 | 14.1 |

[a]Molar ratio of glycol reactant to alkylsulfuric acid reactant.
[b]Conversion based on starting dodecene.
[c]Selectivity is based on dodecene utilization. s-$C_{12}$OH represents secondary dodecanol; s-$C_{12}$EO-1 represents the dodecanol monoethoxylates of formula I wherein x is one; s-$C_{12}$EO-2 represents the diethoxylates of formula I wherein x is two.

I claim as my invention:

1. A process for preparing a detergent-range secondary alkanol alkoxylate product which comprises:
   (a) sulfating, in a sulfation reaction zone, an olefin reactant comprising one or more $C_8$ to $C_{20}$ olefins by reacting said olefin reactant with sulfuric acid of a concentration between about 75 and 100 percent by weight, thereby obtaining a sulfation reaction product mixture containing one or more $C_8$ to $C_{20}$ monoalkyl sulfuric acids,
   (b) introducing said $C_8$ to $C_{20}$ monoalkyl sulfuric acids and a glycol reactant, containing one or more compounds selected from the class consisting of $C_2$ and $C_3$ alkylene glycols and the polyether glycol condensation products of said alkylene glycols, into an alkoxylation reaction zone and reacting at a temperature between about 100° C. and 160° C. for a time between about 0.1 to 4 hours to obtain the desired detergent-range secondary alkanol alkoxylate.

2. A process for preparing a detergent-range secondary alkanol alkoxylate product which comprises:
   (a) sulfating, in a sulfation reaction zone, an olefin reactant comprising one or more $C_8$ to $C_{20}$ olefins by reacting said olefin reactant with sulfuric acid of a concentration between about 75 and 100 percent by weight, thereby obtaining a liquid sulfation reaction product mixture containing one or more $C_8$ to $C_{20}$ monoalkyl sulfuric acids,
   (b) phase separating the sulfation reaction product mixture to obtain an upper liquid phase separation product substantially free of unreacted sulfuric acid,
   (c) reacting, in an alkoxylation reaction zone, at a temperature from about 100° to 160° C. for a time between 0.1 and 4.0 hours, said upper liquid phase with a glycol reactant, containing one or more compounds selected from the class consisting of $C_2$ and $C_3$ alkylene glycols and the polyether glycol condensation products of said alkylene glycols, to yield the desired detergent-range secondary alkanol alkoxylates.

3. A process for preparing a detergent-range secondary alkanol alkoxylate product which comprises:
   (a) sulfating, in a sulfation reaction zone, an olefin reactant comprising one or more $C_8$ to $C_{20}$ olefins by reacting said olefin reactant with sulfuric acid of a concentration between about 75 and 100 percent by weight, thereby obtaining a sulfation reaction product mixture containing one or more $C_8$ to $C_{20}$ monoalkyl sulfuric acids,
   (b) phase separating the sulfation reaction product mixture to obtain an upper liquid phase separation product substantially free of unreacted sulfuric acid,
   (c) reacting in an alkoxylation reaction zone, at a temperature from about 100° to 160° C. for a time between about 0.1 to 4 hours said upper liquid phase separation product with a glycol reactant containing one or more compounds selected from the class consisting of $C_2$ and $C_3$ alkylene glycols and the polyether glycol condensation products of said alkylene glycols, to yield an alkoxylation reaction product mixture containing detergent-range secondary alkanol alkoxylates, $C_8$ to $C_{20}$ olefins, $C_8$ to $C_{20}$ secondary alcohols, glycol compounds, and sulfuric acid,
   (d) phase separating said alkoxylation reaction product mixture to obtain a second upper liquid phase separation product substantially free of sulfuric acid and glycol compounds,
   (e) distilling said second upper liquid phase separation product to produce a distillation bottoms product comprising detergent-range secondary alkanol alkoxylates and an overhead distillation product comprising $C_8$ to $C_{20}$ olefin and $C_8$ to $C_{20}$ secondary alcohol,
   (f) recycling said overhead distillation product to the sulfation reaction zone.

4. The process of claims 1, 2 or 3 in which the glycol reactant contains one or more compounds of the formula

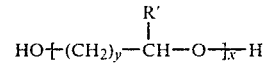

wherein x is an integer from 1 to about 10, y is the integer one or the integer 2, and R' represents, individually in each occurrence, either hydrogen or methyl, with the proviso that R' is hydrogen when y is two.

5. The process of claim 4, in which x represents an integer from 1 to about 4.

6. The process of claim 5, in which the glycol reactant contains one or more compounds selected from the class consisting of $C_2$ and $C_3$ alkylene glycols.

* * * * *